(12) United States Patent
Kataoka et al.

(10) Patent No.: US 9,778,189 B2
(45) Date of Patent: Oct. 3, 2017

(54) CELL OBSERVATION DEVICE, ELECTRICAL STIMULATION DEVICE, AND CELL OBSERVATION METHOD

(71) Applicant: HAMAMATSU PHOTONICS K.K., Hamamatsu-shi, Shizuoka (JP)

(72) Inventors: Takuji Kataoka, Hamamatsu (JP); Taira Ito, Hamamatsu (JP); Natsumi Saito, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 97 days.

(21) Appl. No.: 14/437,964

(22) PCT Filed: Oct. 23, 2013

(86) PCT No.: PCT/JP2013/078717
§ 371 (c)(1),
(2) Date: Apr. 23, 2015

(87) PCT Pub. No.: WO2014/065330
PCT Pub. Date: May 1, 2014

(65) Prior Publication Data
US 2015/0276599 A1   Oct. 1, 2015

(30) Foreign Application Priority Data
Oct. 25, 2012 (JP) .................. 2012-235891

(51) Int. Cl.
*G01N 15/10* (2006.01)
*G01N 15/14* (2006.01)
(Continued)

(52) U.S. Cl.
CPC ..... *G01N 21/6428* (2013.01); *G01N 33/4836* (2013.01); *G01N 33/48728* (2013.01); *G01N 33/5005* (2013.01); *G01N 2201/022* (2013.01)

(58) Field of Classification Search
CPC .......................... C12M 1/34; G01N 33/48728
(Continued)

(56) References Cited

U.S. PATENT DOCUMENTS 4,871,627 A * 10/1989 Strong .................... H01M 2/38
                                              429/176
5,364,521 A * 11/1994 Zimmermann .. G01N 27/44743
                                              204/604
(Continued)

FOREIGN PATENT DOCUMENTS

JP    2001-188044       7/2001
JP    2004-514115 A     5/2004
(Continued)

OTHER PUBLICATIONS

H. Cheng, et al., "Calcium Sparks: Elementary Events Underlying Excitation-Contraction Coupling in Heart Muscle," SCIENCE, vol. 262, No, 5134, Oct. 29. 1993, pp. 740-744, XP055272468.

*Primary Examiner* — Tri Ton
*Assistant Examiner* — Jarreas C Underwood
(74) *Attorney, Agent, or Firm* — Drinker Biddle & Reath LLP

(57) ABSTRACT

A cell observation system 1 is a cell observation system 1 for observing a cell held by a microplate 20 having a plurality of wells 21 arranged therein for holding a sample S including the cell and comprises a microplate holder 11 for mounting the microplate 20, an electrical stimulator 16 arranged with a plurality of electrode pairs 17 including positive and negative electrodes 17b, 17a, and a data analyzer 50 for controlling a position of the electrical stimulator 16 so as to place the electrode pairs 17 within the wells 21 of the microplate 20, while a leading end of the negative electrode 17a on the well 21 side extends longer than a leading end of the positive electrode 17b on the well 21 side.

12 Claims, 16 Drawing Sheets

(51) Int. Cl.
  *G01N 33/48* (2006.01)
  *G01N 21/64* (2006.01)
  *G01N 33/487* (2006.01)
  *G01N 33/483* (2006.01)
  *G01N 33/50* (2006.01)

(58) Field of Classification Search
  USPC .................................. 356/445–448, 450–458
  See application file for complete search history.

(56) References Cited

U.S. PATENT DOCUMENTS

| | | | | |
|---|---|---|---|---|
| 6,470,226 | B1* | 10/2002 | Olesen | G01N 33/48728 435/287.1 |
| 6,783,649 | B2* | 8/2004 | Hedberg | G01N 27/44782 204/451 |
| 7,539,362 | B2* | 5/2009 | Teramura | G01J 3/4535 385/12 |
| 8,658,349 | B2* | 2/2014 | Teich | B01L 3/5025 435/4 |
| 8,994,360 | B2* | 3/2015 | Takeshita | C12M 41/36 324/71.4 |
| 9,079,189 | B2* | 7/2015 | Garcia | B03C 5/005 |
| 9,091,151 | B2* | 7/2015 | Jones | E21B 47/102 |
| 2005/0277183 | A1* | 12/2005 | Lee | C12M 23/12 435/285.2 |
| 2006/0008906 | A1* | 1/2006 | Wills | A61K 35/12 435/451 |
| 2011/0163744 | A1* | 7/2011 | Nakayama | G01N 33/4833 324/249 |
| 2016/0299060 | A1* | 10/2016 | Hokanson | G01N 21/31 |

FOREIGN PATENT DOCUMENTS

| | | |
|---|---|---|
| JP | 2040-147517 | 5/2004 |
| JP | 2005-514909 A | 5/2005 |
| JP | 2007-040753 A | 2/2007 |
| JP | 2007-529215 A | 10/2007 |
| JP | 2007-534927 A | 11/2007 |
| JP | 2011-232056 A | 11/2011 |
| WO | WO-02/08748 A2 | 1/2002 |
| WO | WO 03/006103 | 1/2003 |
| WO | WO 2010/027446 | 3/2010 |
| WO | WO 2011/132586 | 10/2011 |

* cited by examiner

Fig.9
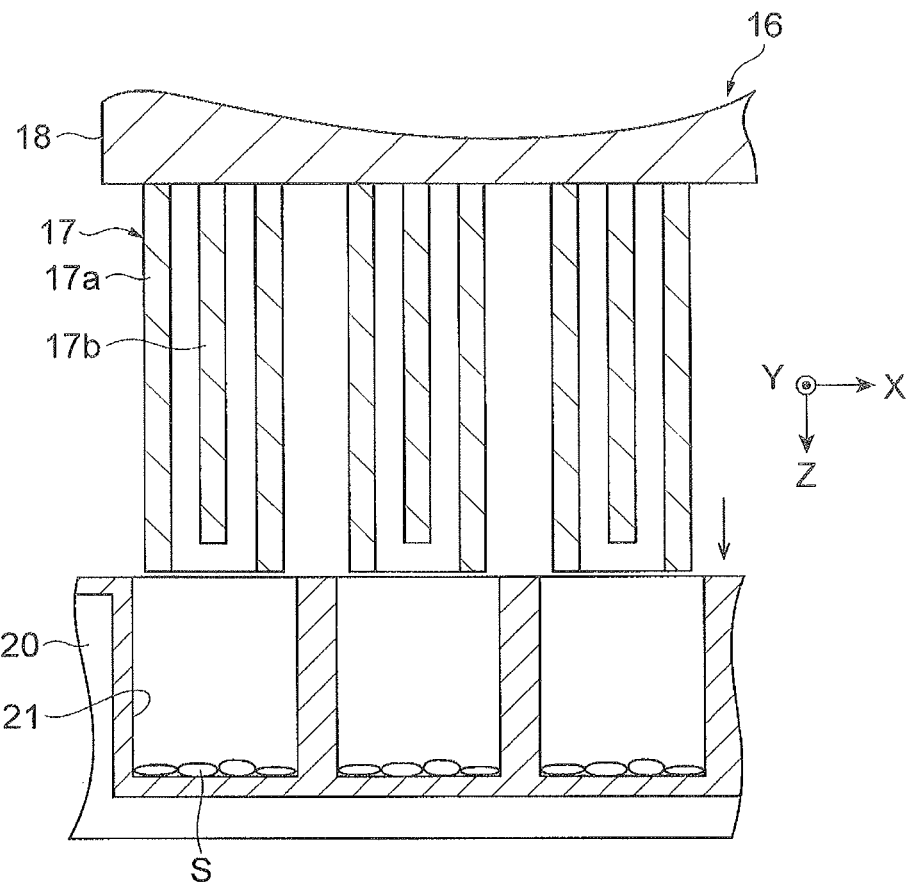
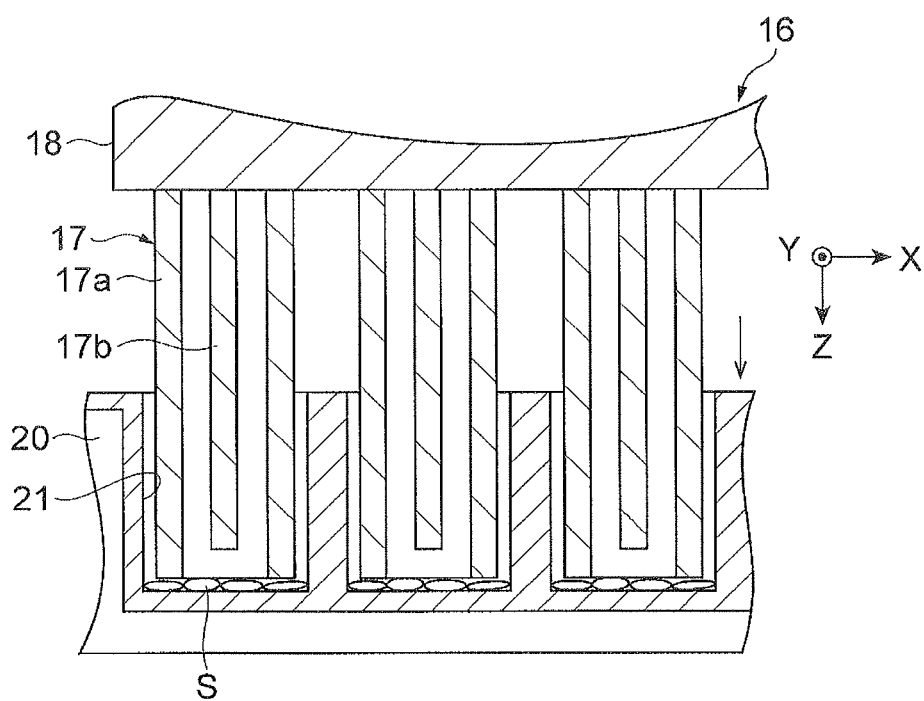

Fig.11
(a) 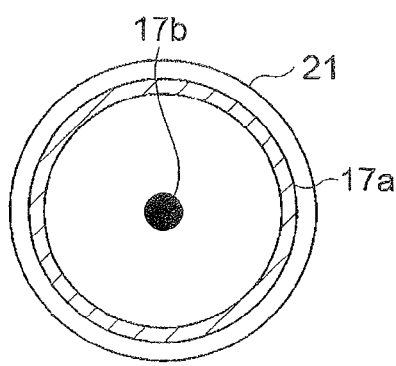 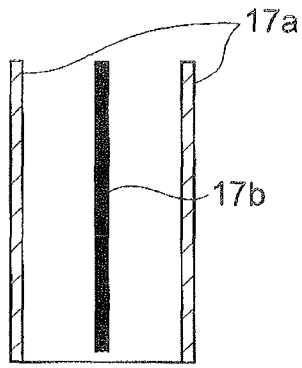
(b) 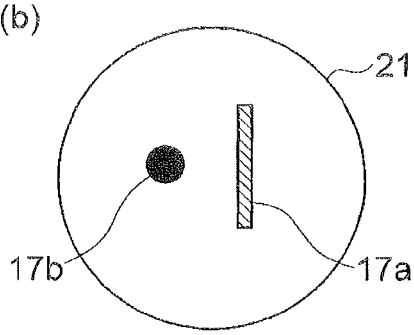 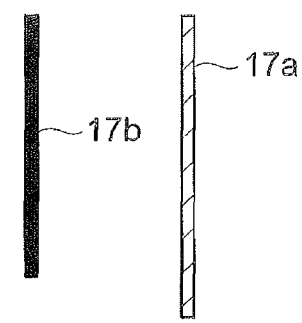
(c) 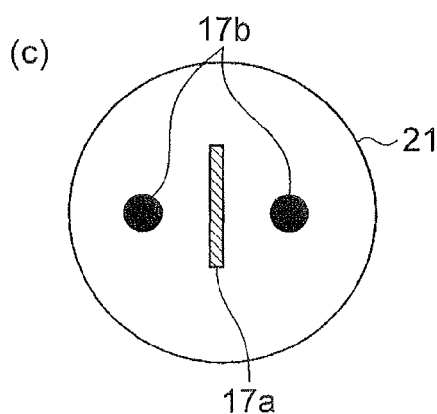 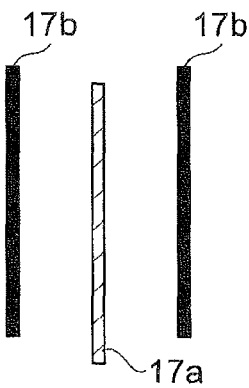
(d) 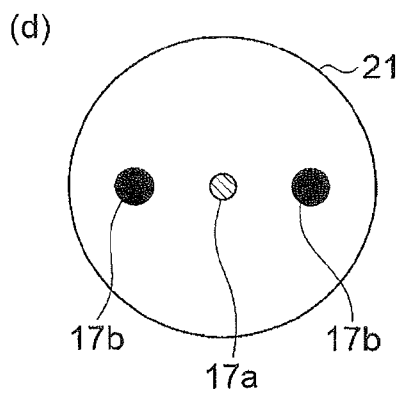 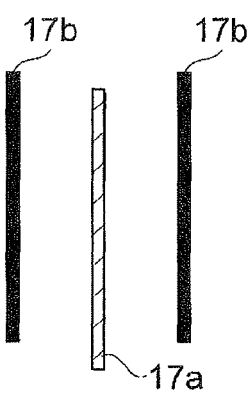

CELL OBSERVATION DEVICE, ELECTRICAL STIMULATION DEVICE, AND CELL OBSERVATION METHOD

TECHNICAL FIELD

The present invention relates to a cell observation system, an electrical stimulation apparatus, and cell observation method for observing a reaction of a sample including a cell in response to electrical stimulation.

BACKGROUND ART

In the field of drug discovery, there are cases where influences of drugs administered to samples such as cells are evaluated by measuring light emitted from the cells. Patent Literature 1 discloses a measurement device comprising an electrode array for generating an electric field in an observation region within a well for a multiwell plate in which a plurality of wells for placing cells therein are arranged. The electrode array is constituted by negative and positive electrodes which are two parallel plate electrodes. Patent Literature 2 discloses a measurement device which monitors a biological response to electric field stimulation of a cell by detecting fluorescence, while this measurement device employs a structure which can place an electrode pair in the form of a coaxial cable constituted by positive and negative electrodes in a well arranged with a cell.

CITATION LIST

Patent Literature

Patent Literature 1: Japanese Translated International Application Laid-Open No. 2007-534927
Patent Literature 2: Japanese Translated International Application Laid-Open No. 2005-514909

SUMMARY OF INVENTION

Technical Problem

In the measurement device disclosed in the above-mentioned Patent Literature 1, the electrode array is placed with a gap from the bottom of the well at the time of measurement. In the measurement device disclosed in the above-mentioned Patent Literature 2, it is considered preferable to use electrode pairs placed away from the cell at the time of measurement.

When placing an electrode away from a cell within a well, however, it is necessary for the distance between the electrode and the cell within the well to be stabilized in order to obtain stable observation results, for which control mechanisms tend to be complicated. This is because the electric field applied to the cell changes greatly when the distance between the electrode and cell varies.

In view of such problems, it is an object of the present invention to provide a cell observation system, electrical stimulation apparatus, and cell observation method which, with a simple structure, can stabilize an electric field applied to a cell within a plurality of arranged holding units.

Solution to Problem

The inventors of the present application have found that, when applying an electric field by an electrode pair including positive and negative electrodes to a cell held by a sample case having a plurality of holding units arranged therein for holding a sample including the cell so as to observe a reaction of the cell thereto, the reaction observed is altered greatly by a minute change in the distance between the positive electrode and cell, thereby designing a structure of the present invention which will be explained later.

Hence, for solving the above-mentioned problems, the cell observation system in accordance with one aspect of the present invention is a cell observation system for observing a cell held by a sample case having a plurality of holding units arranged therein for holding a sample including the cell; the cell observation system comprising a mounting unit for mounting the sample case, an electrical stimulator arranged with a plurality of electrode pairs including positive and negative electrodes, and a position control unit for controlling a position of the electrical stimulator so as to place the electrode pairs within the holding units of the sample case, a leading end of the negative electrode on the holding unit side extending longer than a leading end of the positive electrode on the holding unit side.

The electrical stimulation apparatus in accordance with another aspect of the present invention is an electrical stimulation apparatus, inserted into a sample case having a plurality of holding units arranged therein for holding a sample including a cell, for applying a voltage to the cell, the electrical stimulation apparatus comprising a plurality of electrode pairs, arranged therein, including positive and negative electrodes, the negative electrode having a leading end extending longer than a leading end of the positive electrode.

The cell observation method in accordance with still another aspect of the present invention is a cell observation method for observing a cell held by a sample case having a plurality of holding units arranged therein for holding a sample including the cell; the method comprising a mounting step of mounting the sample case on a mounting unit, and a position control step of controlling a position of an electrical stimulator arranged with a plurality of electrode pairs including positive and negative electrodes so as to place the electrode pairs within the holding units of the sample case, a leading end of the negative electrode on the holding unit side extending longer than a leading end of the positive electrode on the holding unit side.

In the foregoing cell observation system, electrical stimulation apparatus, and cell observation method, electrode pairs including positive and negative electrodes are placed within a plurality of holding units arranged in a sample case, whereby the electrode pairs can apply an electric field to a sample including a cell. Here, in the positive and negative electrodes constituting the electrode pair, the leading end of the negative electrode extends longer than that of the positive electrode, whereby inserting the electrode pair into the holding unit such that the leading end of the negative electrode comes into contact with the sample at the bottom part of the holding unit can stabilize the distance between the leading end of the positive electrode and the sample at a predetermined distance. As a consequence, just providing a simple position control mechanism can stabilize the electric field applied from the electrode pair to the sample, whereby uniform observation results concerning the sample can be obtained.

Advantageous Effects of Invention

With a simple structure, the present invention can stabilize an electric field applied to a cell within a plurality of arranged holding units.

BRIEF DESCRIPTION OF DRAWINGS

FIG. 9 is a partially broken sectional view illustrating how a data analyzer 50 in FIG. 1 controls the position of an electrical stimulator 16;

FIG. 11 is a sectional view illustrating structures of electrode pairs 17 in accordance with modified examples of the embodiment;

DESCRIPTION OF EMBODIMENTS

Figure 1:
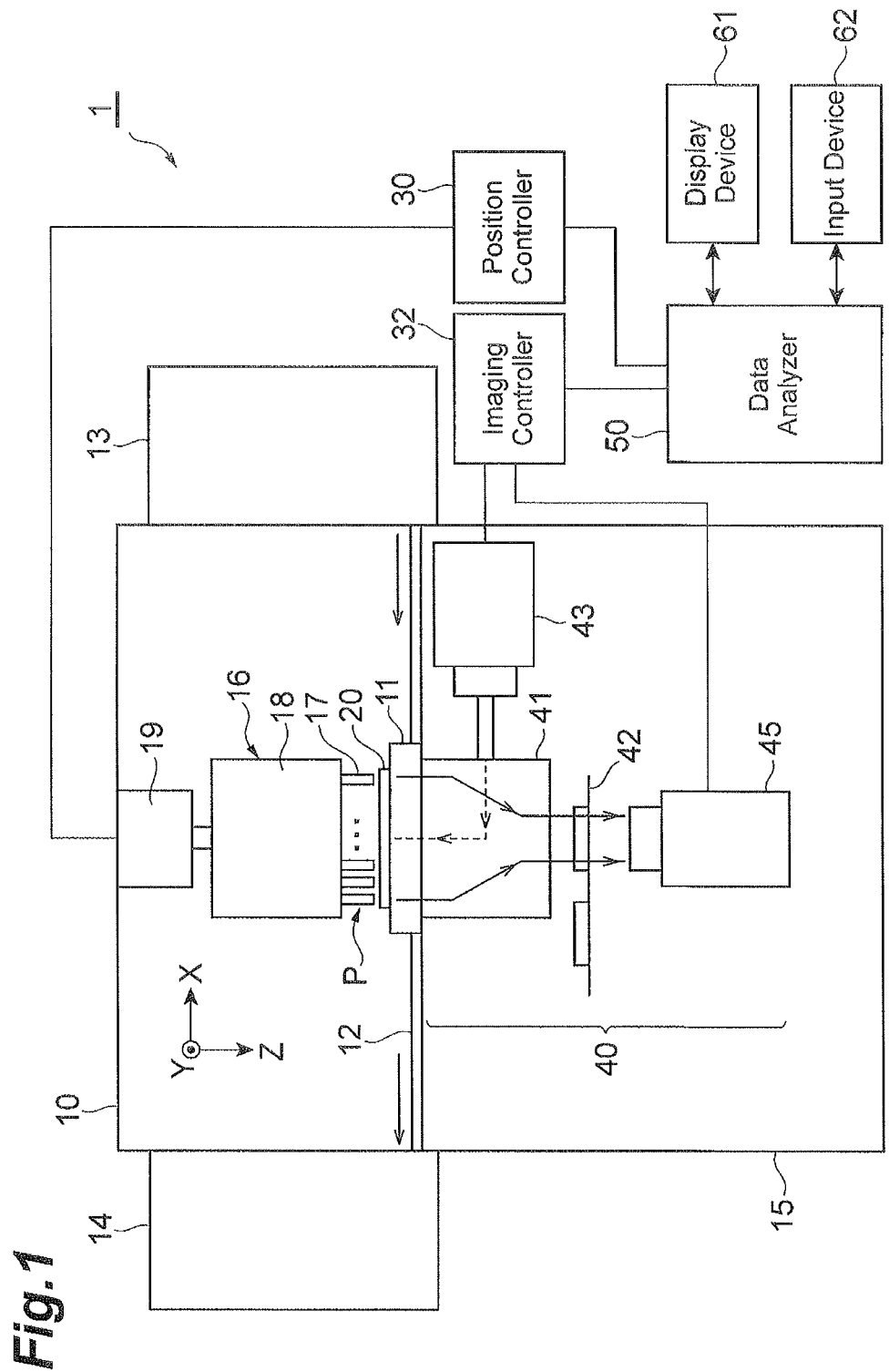
FIG. 1 is a diagram illustrating a schematic structure of a cell observation system 1 in accordance with a preferred embodiment of the present invention.

In the following, embodiments of the cell observation system, the electrical stimulation apparatus, and cell observation method in accordance with the present invention will be explained in detail with reference to the accompanying drawings. In the explanation of drawings, the same constituents will be referred to with the same signs while omitting their overlapping descriptions. The drawings are made for explanation and emphasize parts to be explained in particular. Therefore, members in the drawings are not always to scale.

Figure 2:
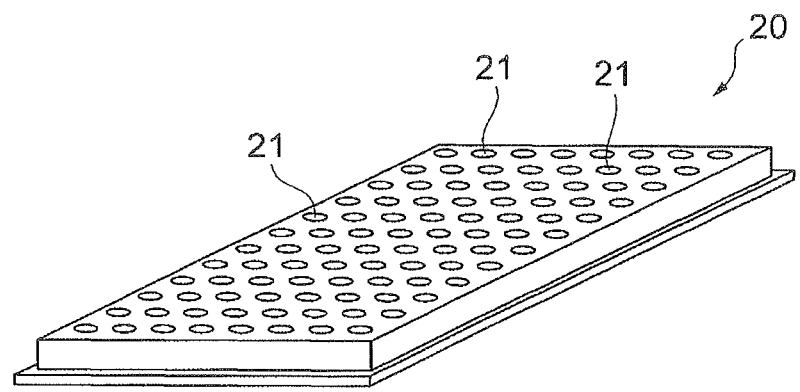
FIG. 2 is a perspective view illustrating a structure of a microplate 20 in FIG. 1.
Figure 3:
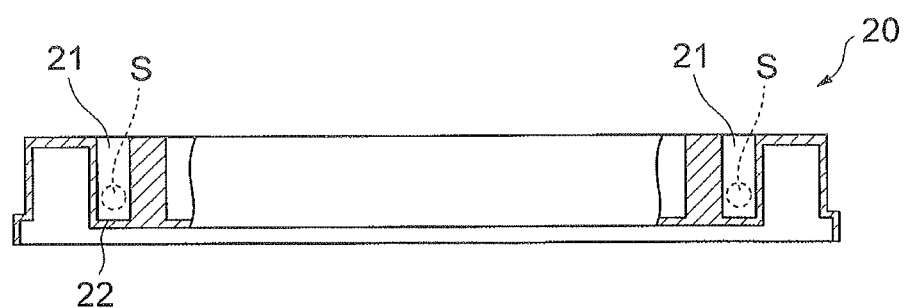
FIG. 3 is a side sectional view illustrating a cross-sectional structure of the microplate 20 in FIG. 1.

FIG. 1 is a structural diagram schematically illustrating an embodiment of a cell observation system 1 in accordance with the present invention. FIG. 2 is a perspective view illustrating an example of the structure of a microplate 20. FIG. 3 is a side sectional view illustrating a cross-sectional structure of the microplate 20 in FIG. 2. The cell observation system 1 in accordance with this embodiment is a device, which uses the microplate 20 as a sample case, for measuring fluorescence from a sample S placed at a measurement position P while being held by the microplate 20.

The sample S includes a predetermined cell. An example of the predetermined cell is a neuron. The cell observation system, electrical stimulation apparatus, and cell observation method in this embodiment are employable not only for fluorescence measurement, but also for light measurement for measuring light in general, such as phosphorescence and luminescence, for example, emitted from samples. In the following, the structure of the cell observation system 1 will be explained.

The cell observation system 1 illustrated in FIG. 1 comprises a data acquisition device 10, a position controller (position control unit) 30, an imaging controller 32, and a data analyzer 50. The data acquisition device 10 has a dark box 15 for containing therewithin the microplate 20 holding a cell subjected to fluorescence measurement and a moving image acquisition unit 40 which is installed within the dark box 15 and used for measuring fluorescence from the sample S placed at the measurement position P.

As illustrated in FIGS. 2 and 3, the microplate 20 used as the sample case in this embodiment is a planar member in which a plurality of wells (holding units) 21 are arranged in a two-dimensional array, which is constructed such that the sample S can be held in each of the plurality of wells 21. In the structural example illustrated in FIG. 2, 8×12=96 circular wells 21 are arranged in a two-dimensional array as a plurality of wells 21. Examples of cross-sectional forms of the wells 21 include circles, ellipses, and rectangles. The microplate 20 has a bottom face 22 formed from a material which can transmit therethrough excitation light, with which the sample S is irradiated for fluorescence measurement, and fluorescence emitted from the sample S. In general, it is sufficient for the bottom face 22 of the microplate 20 in the cell observation system 1 to be formed from a material which can transmit therethrough light emitted from the sample S to be measured.

Within the dark box 15, the microplate 20 is mounted on a microplate holder (mounting unit) 11 having an opening for observing fluorescence. A microplate transfer mechanism 12 for transferring the microplate 20 and microplate holder 11 in a predetermined direction (from the right side to the left side in FIG. 1) within the dark box 15 is also installed within the dark box 15.

Installed on one side serving as the inlet side of the dark box 15 in the transfer direction of the microplate 20 in the transfer mechanism 12 is an inlet microplate stocker 13 for stocking a predetermined number of (e.g., 25) microplates 20 holding the sample S before measurement. Installed on the other side serving as the outlet side of the dark box 15 in the transfer direction of the microplate 20 is an outlet microplate stocker 14 for stocking the microplates 20 after measurement.

In this structure, the microplate 20 taken from the inlet microplate stocker 13 into the dark box 15 is held by the microplate holder 11 and transferred by the transfer mechanism 12. The microplate 20 is once stopped at the measurement position P, and light measurement necessary for the sample S held by the microplate 20 is performed in this state. After the measurement is completed, the microplate 20 is transferred by the transfer mechanism 12 again, so as to be taken out to the outlet microplate stocker 14. In FIG. 1, specific structures for taking in, transferring, and taking out the microplate 20 are not depicted for the transfer mechanism 12 and stockers 13, 14.

Installed above the measurement position P where the microplate 20 and sample S are placed at the time of performing fluorescence measurement is an electrical stimulator (electrical stimulation apparatus) 16 to be inserted into the wells 21 of the microplate 20 in order to generate an electric field in the sample S. Installed under the measurement position P is the moving image acquisition unit (light detection unit) 40 used for detecting fluorescence emitted through the bottom face 22 of the microplate 20 from the sample S contained within the wells 21.

The moving image acquisition unit 40 is a moving image acquisition means which detects a two-dimensional optical image representing a two-dimensional optical intensity distribution of the microplate 20 including light emitted from the sample S held within the wells 21 of the microplate 20 and acquires moving image data of the two-dimensional optical image. The two-dimensional optical image to be detected may be an optical intensity distribution including light emitted from the sample S held within at least one well 21. The moving image acquisition unit 40 is constituted by an imaging device 45, a light-guiding optical system 41, an optical filter unit 42, and an excitation light source 43. The imaging device 45 has a two-dimensional pixel structure in which a plurality of pixels are arranged two-dimensionally and detects a fluorescence image which is a two-dimensional light detection image caused by the fluorescence emitted from the sample S. As the imaging device 45, a highly sensitive CCD camera or CMOS imaging camera can be used, for example. If necessary, an image intensifier, a relay lens, and the like may be placed in front of the camera, so as to construct the moving image acquisition unit 40. The image acquisition unit 40, which may acquire still images, has a function as an image acquisition unit for acquiring a moving image and/or a still image.

The light-guiding optical system 41 is installed between the measurement position P where the microplate 20 is placed and the imaging device 45. The light-guiding optical system 41 is an optical system which guides to the imaging device 45 a two-dimensional optical image of the microplate 20 holding the sample S in each of the plurality of wells 21 as seen from the bottom face 22 side. A specific structure of the light-guiding optical system 41 may be constructed as appropriate by optical elements which can achieve necessary functions (e.g., condensing function and optical image reducing function) according to the structures of the microplate 20 and imaging device 45 and the like. An example of such optical elements is a tapered fiber (see Japanese Patent Application Laid-Open No. 2001-188044). The light-guiding optical system 41 may also be constructed such as to use a light-guiding member having irregularities (see Japanese Patent Application Laid-Open Nos. 2010-230397 and 2010-230396).

In FIG. 1, the optical filter unit 42 adapted to place an optical filter onto the light-guiding path for fluorescence, switch it, and so forth when necessary is further installed between the light-guiding optical system 41 and imaging device 45. However, the optical filter unit 42 may be omitted when unnecessary.

The excitation light source 43 is an excitation light supply means for supplying the sample S with excitation light for fluorescence measurement. A specific structure of the excitation light source 43, an example of which is constituted by an illumination light source for supplying light and an optical filter unit for selecting or switching a wavelength of the excitation light, may be constructed as appropriate according to the kind of the sample S subjected to fluorescence measurement, the wavelength of the excitation light irradiating the sample S, and the like. The excitation light source 43 may be omitted when no supply of excitation light is necessary according to the kind of light measurement performed for the sample S.

In this embodiment, the light-guiding optical system 41 is constructed as an optical system which can guide the two-dimensional optical image from the microplate 20 and sample S to the imaging device 45 and the excitation light from the excitation light source 43 to the sample S. For example, such an optical system can be constructed by using a dichroic mirror which transmits therethrough the fluorescence from the microplate 20 and reflects the excitation light from the excitation light source 43. FIG. 1 schematically illustrates optical paths of the fluorescence and excitation light in the light-guiding optical system 41 with solid and broken lines, respectively.

Figure 4:
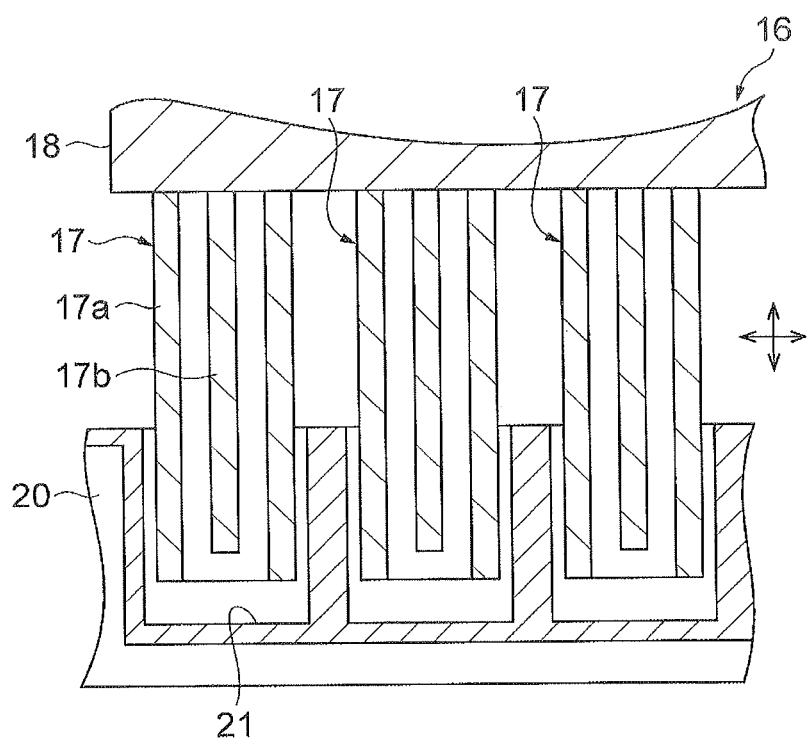
FIG. 4 is a partially broken sectional view of an electrical stimulator 16 in FIG. 1.

The structure of the electrical stimulator 16 will now be explained in detail. FIG. 4 is a partially broken sectional view of the electrical stimulator 16 in a state inserted in the microplate 20. The electrical stimulator 16 has a structure in which a plurality of electrode pairs 17 extending vertically toward the microplate 20 are secured to a base part 18 so as to be arranged two-dimensionally. Specifically, the electrode pairs 17 are arranged two-dimensionally so as to correspond to the two dimensional array arrangement of the plurality of wells 21 of the microplate 20 and extend while facing the wells 21 of the microplate 20. Each electrode pair 17 is constituted by a negative electrode 17a having a cylindrical form surrounding a positive electrode 17b with an open leading end and the rod-shaped (e.g., columnar) positive electrode 17b inserted into the negative electrode 17a so as to be placed on the center axis of the negative electrode 17a, while the negative electrode 17a has an outer diameter smaller than the inner diameter of the well 21. The cylindrical form of the negative electrode 17a may have either a circular or elliptical cross section. The electrode pair 17 also has such a structure that the leading end of the opening of the negative electrode 17a on the well 21 side extends longer by a predetermined distance (e.g., within the range of at least 1 μm but not more than 1.0 mm) than the leading end of the positive electrode 17b on the well 21 side, i.e., such a form that the distance from the base part 18 to the leading end of the positive electrode 17b is shorter by the predetermined distance than the distance from the base part 18 to the leading end of the negative electrode 17a. This allows the rod-shaped positive electrode 17b to be contained within the negative electrode 17a having the cylindrical form. This also forms a structure in which the positive electrode 17b does not project from the leading end of the negative electrode 17a, and the leading end of the negative electrode 17a and that of the positive electrode 17b are not flush with each other. The electrode pair 17 is not limited to one in which each of the negative and positive electrodes 17a, 17b is constituted by one member, but one or both of them may be constituted by a plurality of members.

The electrical stimulator 16 is also provided with a shifter mechanism 19 for supporting the electrode pairs 17 with the base part 18 interposed therebetween. The shifter mechanism 19, which is a driving mechanism for moving the electrode pairs 17 toward or away from the microplate 20 (in the Z direction in FIG. 1) and in directions along the bottom face 22 of the microplate 20 (in directions along a plane including the X and Y axes in FIG. 1), drives the electrode pairs 17 so as to place them into their opposing wells 21 when observing the sample S and separate them from within the wells 21 when the observation of the sample S is completed.

Coupled to thus constructed data acquisition device 10 are the position controller (position control unit) 30 and imaging controller 32. The position controller 30 is electrically coupled to the shifter mechanism 19 and controls the shifter mechanism 19 such that the electrode pairs 17 are placed within the wells 21 of the microplate 20 when starting light measurement of the sample S. The position controller 30 is also electrically coupled to the electrode pairs 17 so as to apply voltages to the negative and positive electrodes 17a, 17b, respectively, such that a potential difference occurs between the negative and positive electrodes 17a, 17b of the electrode pairs 17. The imaging controller 32 controls the irradiation with the excitation light by the excitation light source 43 and the capture of the two-dimensional fluorescence image in the microplate 20 by the imaging device 45.

The data analyzer 50 is further coupled to the position controller 30 and imaging controller 32. The data analyzer 50 is an analysis processing means which obtains through the imaging controller 32 the moving image data including the light detection image acquired by the moving image acquisition unit 40 and performs analysis processing for the moving image data. The data analyzer 50 also controls the fluorescence measurement for the sample S in the cell observation system 1 by regulating operations of individual parts of the data acquisition device 10 through the position controller 30 and imaging controller 32 (as will be explained later in detail). In FIG. 1, a display device 61 for displaying measurement results and the like and an input device 62 used for inputting data and instructions required for fluorescence measurement are coupled to the data analyzer 50.

Figure 5:
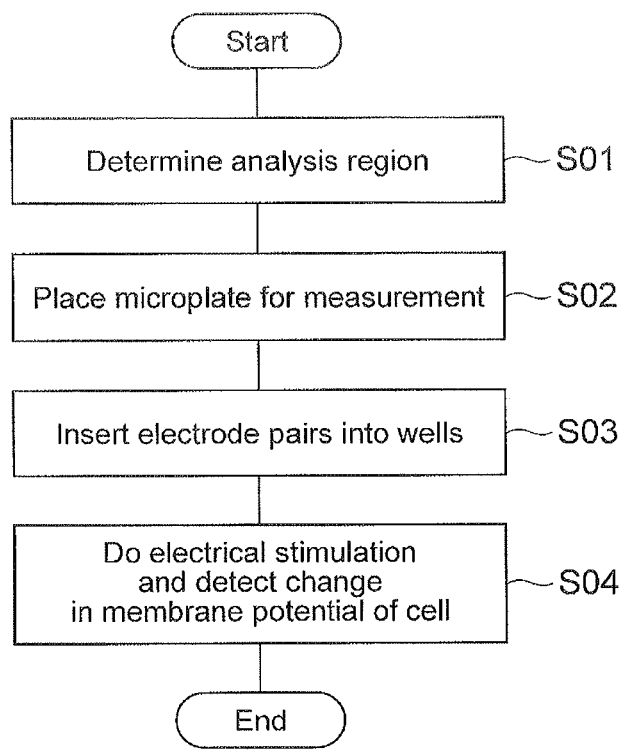
FIG. 5 is a flowchart illustrating operations of the cell observation system 1 at the time of measuring light from a sample S.
Figure 6:
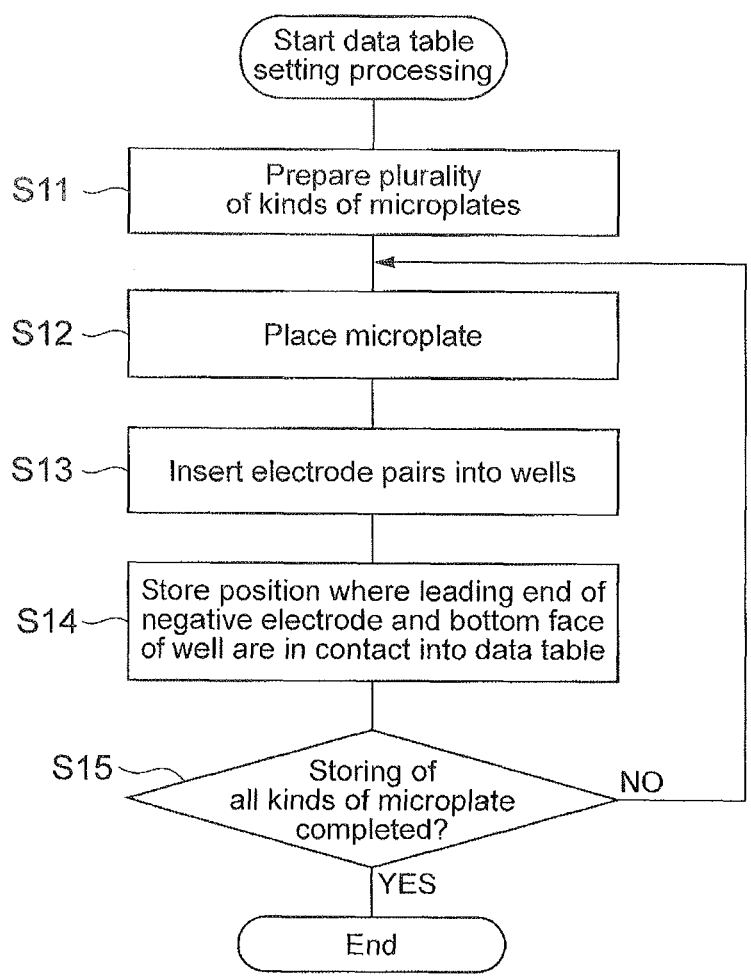
FIG. 6 is a flowchart illustrating a procedure of processing for setting a position setting data table which is executed before the light measurement processing in FIG. 5.

With reference to FIGS. 5 and 6, the cell observation method in accordance with this embodiment will now be set forth in detail while explaining operations by the cell observation system 1 at the time of measuring light from the sample S. FIG. 5 is a flowchart illustrating operations of the cell observation system 1 at the time of measuring light from the sample S, while FIG. 6 is a flowchart illustrating a procedure of processing for setting a position setting data table which is executed before the light measurement.

First, a trigger to start light measurement of a cell is inputted through the input device 62, whereupon the data analyzer 50 determines an analysis region in a two-dimensional optical image or still image included in the moving image data to be processed (step S01: analysis region determination step). The analysis region is set according to data in which a region including an area directly under the positive electrode 17b in a reflected image of each well 21 has been stored beforehand. Subsequently, while being mounted on the microplate holder 11, the microplate 20 to be measured holding the sample S within the microplate stocker 13 is transferred by the microplate transfer mechanism 12 to the measurement position P within the dark box 15 (step S02: mounting step). Then, the data analyzer 50 controls the position of the electrical stimulator 16 by utilizing the shifter mechanism 19, so as to insert the leading ends of a plurality of electrode pairs 17 into their corresponding wells 21 of the microplate 20 (step S03: position control step). At this time, with reference to positional data corresponding to the kind of the currently in-use microplate 20 in a position setting data table stored beforehand, the data analyzer 50 controls positions of the electrode pairs 17 such that the leading ends of the negative electrodes 17a in the electrode pairs 17 come into contact with the bottom face 22 of the microplate 20. This places the positive electrodes 17b in a state where their leading ends are separated from the bottom faces of the wells 21 by about a predetermined distance (e.g., at least 1 μm but not more than 1.0 mm) corresponding to their difference in length from the negative electrodes 17a.

Thereafter, the data analyzer 50 controls the position controller 30, so as to supply a voltage to the electrode pairs 17, thereby generating an electric field within the wells 21 of the microplate 20 (provision of electrical stimulation). In the state where the electric field is generated, the moving image acquisition unit 40 detects a two-dimensional optical image of the microplate 20 including fluorescence emitted from the sample S held within the wells 21, whereby the data analyzer 50 acquires moving image data representing the two-dimensional optical image. The moving image acquisition unit 40 has a frame rate which is set higher than the frequency at which the voltage is applied. For the two-dimensional optical image included in the acquired moving image data, the data analyzer 50 analyzes the optical intensity in an analysis region which is set in a part of a region facing the electrode pairs 17 of the microplate 20 on the microplate holder 11, whereby analysis information concerning the sample S is obtained and outputted to the display device 61 (step S04: light detection step and information analysis step). Since the cell in the sample S is provided with a membrane potential-sensitive fluorescent dye, a change in the membrane potential accompanying opening/closing of an ion channel of the cell is seen as a change in intensity of fluorescence when electrical stimulation is applied thereto. As techniques for analyzing optical intensity in such an analysis region, those calculating the amplitude of change, ratio of change, peak period, number of peaks, peak time, rise time, fall time, peak fluctuation range, and the like in pixel values in the analysis region as evaluation values may be considered.

Referring now to FIG. 6, the procedure of processing for setting the position setting data table executed before the light measurement processing in FIG. 5 will be explained. First, a plurality of kinds of microplates 20 each having empty wells 21 are prepared within the microplate stocker 13 (step S11). Subsequently, while being mounted on the microplate holder 11, one kind of microplate 20 in the plurality of kinds of microplates 20 is transferred by the microplate transfer mechanism 12 to the measurement position P within the dark box 15 (step S12). Thereafter, by using the input device 62 of the data analyzer 50, positional data for adjusting the position of the electrical stimulator 16 is inputted to the position controller 30, whereby the leading ends of the plurality of electrode pairs 17 are inserted into their corresponding wells 21 of the microplate 20 (step S13). Here, the position of the electrical stimulator 16 is adjusted such that the leading end of the negative electrode 17a of each electrode pair 17 comes into contact with the bottom face 22 of its opposing well 21. The positional data inputted by the input device 62 at that time is stored into the position setting data table within the data analyzer 50 in association with data concerning the kind of the microplate 20 (step S14). The processing of the foregoing steps S12 to S14 is repeated for all the kinds of microplates 20 (step S15), whereby the setting of the position setting data table is completed.

Figure 7:
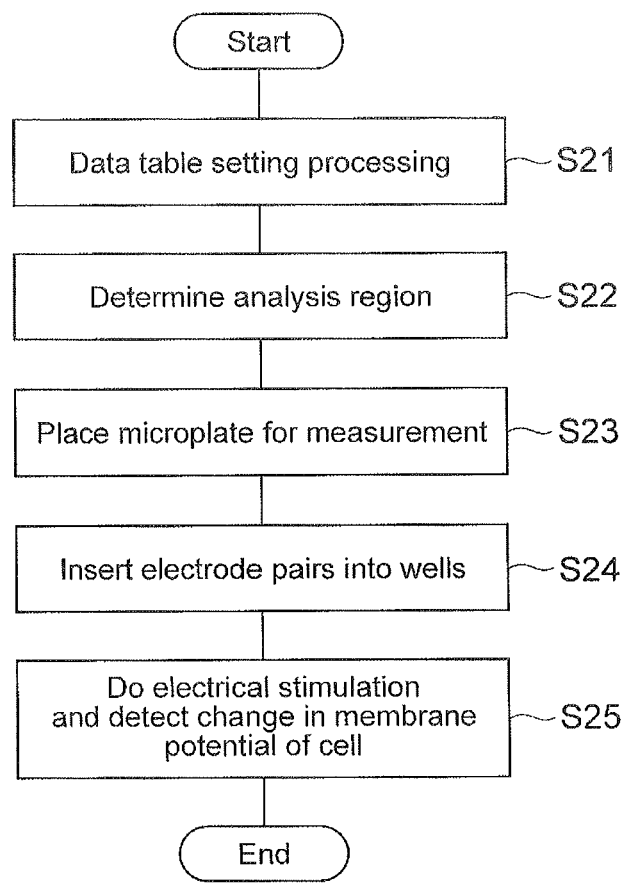
FIG. 7 is a flowchart illustrating another operation of the cell observation system 1 in FIG. 1 at the time of measuring light from the sample S.

The cell observation system 1 may set the position setting data table in the middle of the light measurement operation for the sample S. FIG. 7 illustrates the operation procedure of the cell observation system 1 at the time of measuring light from the sample S in such a case.

In this case, a trigger to start light measurement of a cell is inputted through the input device 62, whereupon the position setting data table is set for adjusting the position of the electrical stimulator 16 (step S21). Subsequently, the data analyzer 50 determines an analysis region in a two-dimensional optical image included in the moving image data to be processed (step S22: analysis region determination step). The analysis region is set according to data in which a region including an area directly under the positive electrode 17*b* in the reflected image of each well 21 has been stored beforehand. Subsequently, while being mounted on the microplate holder 11, the microplate 20 to be measured holding the sample S within the microplate stocker 13 is transferred by the microplate transfer mechanism 12 to the measurement position P within the dark box 15 (step S23: mounting step). Then, the data analyzer 50 controls the position of the electrical stimulator 16 by utilizing the shifter mechanism 19, so as to insert the leading ends of the plurality of electrode pairs 17 into their corresponding wells 21 of the microplate 20 (step S24: position control step). At this time, with reference to the positional data of the position setting data table stored at the step S21, the data analyzer 50 controls the positions of the electrode pairs 17 such that the leading ends of the negative electrodes 17*a* of the electrode pairs 17 come into contact with the bottom face 22 of the microplate 20. In practice, however, the wells 21 of the microplate 20 hold the sample S, whereby the leading ends of the negative electrodes 17*a* of the electrode pairs 17 may fail to come into contact with the bottom face 22 of the microplate 20. This places the positive electrodes 17*b* in a state where their leading ends are separated from the bottom faces of the wells 21 by about a predetermined distance (e.g., 1 µm to 1.0 mm) corresponding to their difference in length from the negative electrodes 17*a*.

Thereafter, the data analyzer 50 controls the position controller 30, so as to supply voltages to the electrode pairs 17, thereby generating an electric field within the wells 21 of the microplate 20 (provision of electrical stimulation). In the state where the electric field is generated, the moving image acquisition unit 40 detects a two-dimensional optical image of the microplate 20 including fluorescence emitted from the sample S held within the wells 21, whereby the data analyzer 50 acquires moving image data representing the two-dimensional optical image. For the two-dimensional optical image included in the acquired moving image data, the data analyzer 50 analyzes the optical intensity in an analysis region which is set in a part of a region facing the electrode pairs 17 of the microplate 20 on the microplate holder 11, whereby analysis information concerning the sample S is obtained and outputted to the display device 61 (step S25: light detection step and information analysis step).

Figure 8:
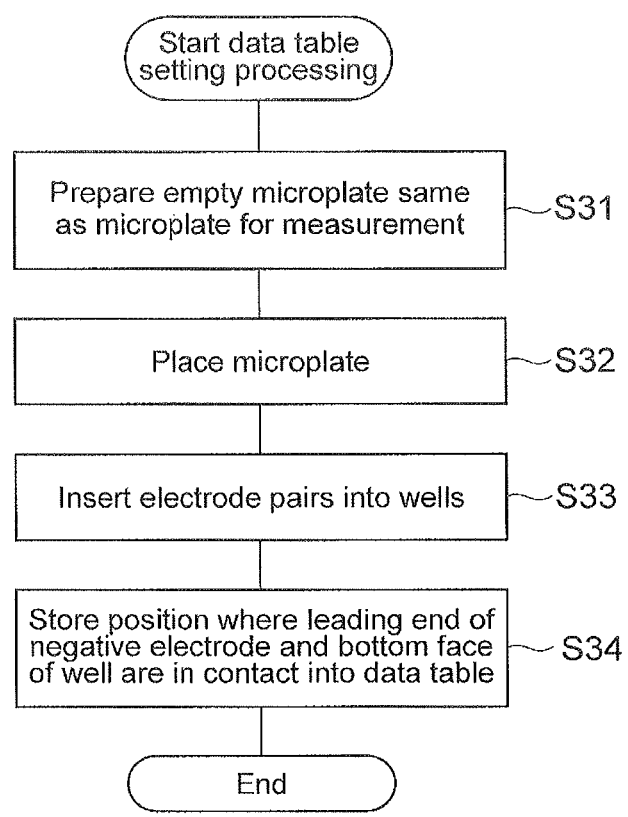
FIG. 8 is a flowchart illustrating a procedure of processing for setting the position setting data table which is executed at step S21 in FIG. 7.

Referring now to FIG. 8, the procedure for setting the position setting data table executed at the step S21 in FIG. 7 will be explained in detail. First, the microplate 20 of the same kind as that of the microplate 20 for measurement is prepared with its wells 21 empty within the microplate stocker 13 (step S31). Subsequently, while being mounted on the microplate holder 11, the microplate 20 is transferred by the microplate transfer mechanism 12 to the measurement position P within the dark box 14 (step S32). Thereafter, by using the input device 62 of the data analyzer 50, positional data for adjusting the position of the electrical stimulator 16 is inputted to the position controller 30, whereby the leading ends of the plurality of electrode pairs 17 are inserted into their corresponding wells 21 of the microplate 20 (step S33). Here, the position of the electrical stimulator 16 is adjusted such that the leading end of the negative electrode 17*a* of each electrode pair 17 comes into contact with the bottom face 22 of its opposing well 21. The positional data inputted by the input device 62 at that time is temporarily stored into the position setting data table within the data analyzer 50 (step S34) in order to be referred to at the step S24. The foregoing completes the setting of the position setting data table.

Figure 10:
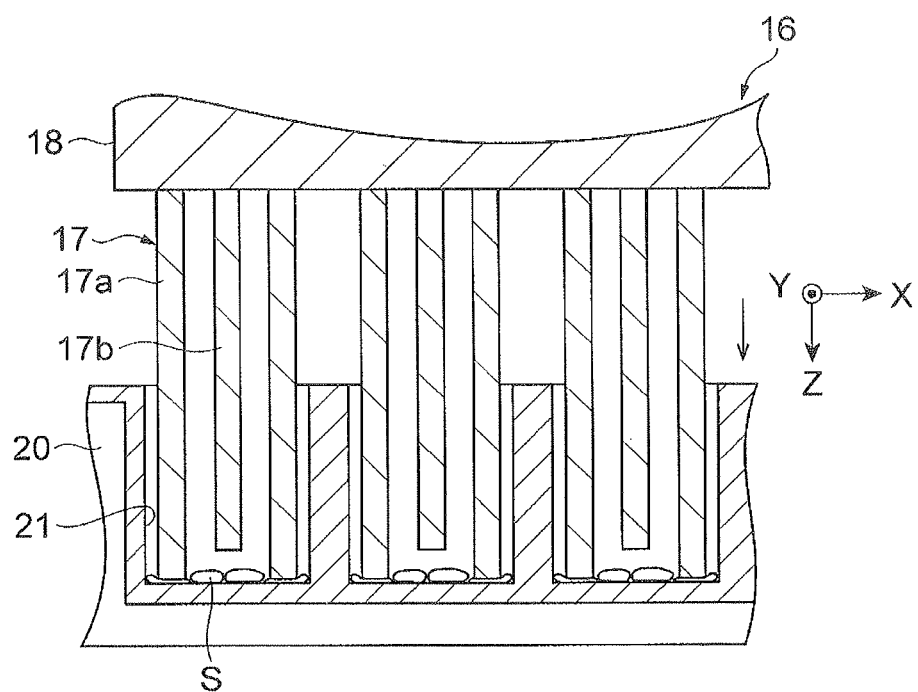
FIG. 10 is a partially broken sectional view illustrating how the data analyzer 50 in FIG. 1 controls the position of the electrical stimulator 16.

The above-mentioned position control of the electrical stimulator 16 by the data analyzer 50 at the step S03 (FIG. 5) and step S24 (FIG. 7) at the time when the cell observation system 1 measures light from the sample S will now be explained in detail. At the steps S03 and S24, as illustrated in FIG. 9(*a*), the data analyzer 50 initially refers to the position setting data table, so as to move the electrical stimulator 16 such that the positions of the leading ends of the plurality of electrode pairs 17 in directions along the bottom face 22 of the microplate 20 (directions along the X-Y plane) oppose their corresponding wells 21. Then, the data analyzer 50 further refers to the position setting data table, so as to move down the electrical stimulator 16 in the Z direction until the leading ends of the negative electrodes 17*a* of the electrode pairs 17 come into contact with the sample S reserved on the bottom faces of the wells 21 as illustrated in FIG. 9(*b*). Here, the positional data in the Z direction stored in the position setting data table is set in consideration of a minute length (e.g., a distance of at least 0.1 mm but not more than 0.2 mm) by which the sample S is held between the leading end of the negative electrode 17*a* and the bottom face of the well 21. Thereafter, as illustrated in FIG. 10, the data analyzer 50 moves down the electrical stimulator 16 in the Z direction until the leading ends of the negative electrodes 17*a* of the electrode pairs 17 come into contact with the bottom faces of the wells 21 by pressing the sample S reserved on the bottom faces. By thus controlling the positions of the electrode pairs 17 so as to press the bottom faces further by a distance of about at least 0.1 mm but not more than 0.2 mm from the positions acquired beforehand, even when the bottom faces of a plurality of wells 21 are located at uneven positions, the leading ends of the negative electrodes 17*a* can be brought into contact with the bottom faces of all the wells 21.

In the cell observation system 1 and cell observation method by the cell observation system 1 explained in the foregoing, the electrode pairs 17 including the positive and negative electrodes 17*b*, 17*a* are placed in a plurality of wells 21 arranged in the microplate 20, so as to make an electric field applicable to the sample S including a cell. Here, in the positive and negative electrodes 17*b*, 17*a* constituting each electrode pair 17, the leading end of the negative electrode 17*a* extends longer than the leading end of the positive electrode 17*b*, whereby the distance between the leading end of the positive electrode 17*b* and the sample S can be stabilized at a predetermined distance (e.g., a distance of at least 1 µm but not more than 1 mm) by inserting the electrode pair 17 into the well 21 such that the leading end of the negative electrode 17*a* comes into contact with the sample S at the bottom part of the well 21. As a consequence, just providing a simple position control mechanism can stabilize the electric field applied from the electrode pairs 17 to the sample S, whereby uniform observation results concerning the sample S can be obtained. Such a structure brings the negative electrodes 17*a* into contact with the sample S, whereby the sample S can be provided with an appropriate potential difference.

In the above-mentioned cell observation system 1, the data analyzer 50 controls the positions of the negative electrodes 17a such that their leading ends on the well 21 side come into contact with the bottom faces of the wells 21, which can stabilize the distance from the leading ends of the positive electrodes 17b to the sample S at a predetermined distance, whereby just providing a simple position control mechanism can stabilize the electric field applied from the electrode pairs 17 to the sample S.

Since each positive electrode 17b is a rod-shaped electrode, a region with a strong electric field on the bottom face 22 of the well 21 can be limited to an area near the positive electrode 17b. This can yield highly sensitive observation results concerning the sample S.

The present invention is not limited to the above-mentioned embodiment.

The structure of the electrode pair 17 in the electrical stimulator 16 is not limited to the coaxial form but can employ various forms. The data analyzer 50 can set the analysis region according to the structure of the electrode pair 17.

Figure 12:
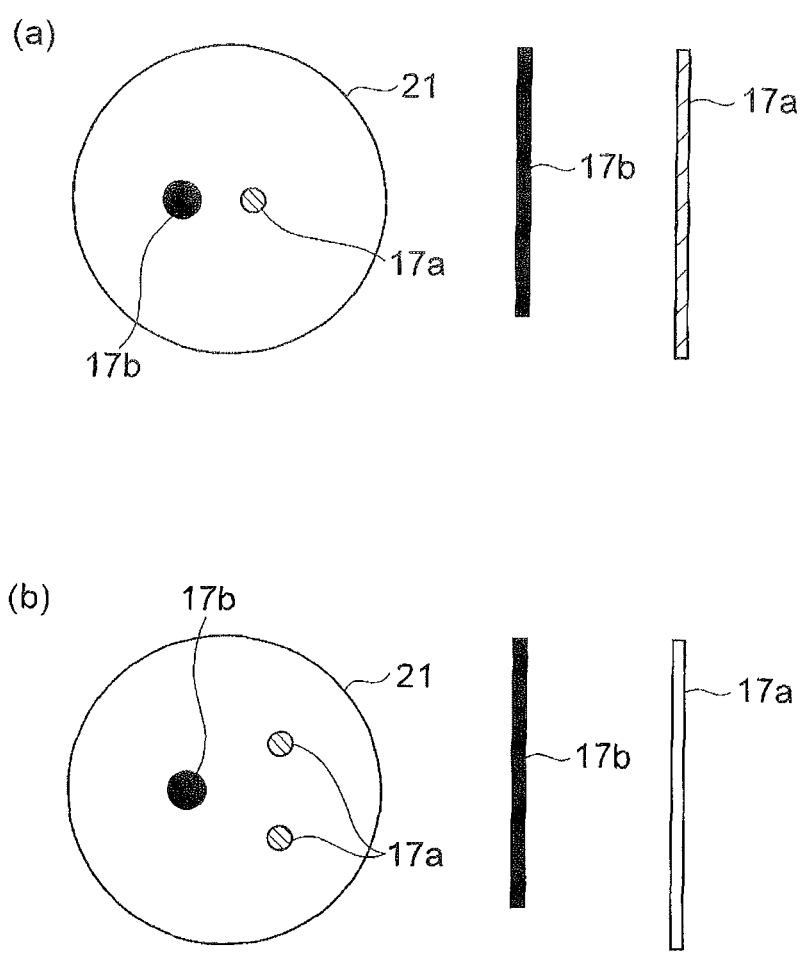
FIG. 12 is a sectional view illustrating structures of electrode pairs 17 in accordance with modified examples of the embodiment.

FIGS. 11 and 12 illustrate structures of electrode pairs 17 in accordance with modified examples of this embodiment. Each of FIGS. 11(a) to (d) and FIGS. 12(a) and (b) illustrates cross sections of the electrode pair 17 taken perpendicularly to and along the bottom face of the microplate 20 on the right and left sides, respectively, together with the well 21. As these diagrams represent, the electrode pair 17 can employ not only the coaxial form illustrated in FIG. 11(a), but also a structure of a combination of a rod-shaped positive electrode 17b and a planar negative electrode 17a facing it as illustrated in FIG. 11(b), a structure in which two rod-shaped positive electrodes 17b face each other across a planar negative electrode 17a in parallel as illustrated in FIG. 11(c), a structure in which two rod-shaped positive electrodes 17b face each other across a rod-shaped negative electrode 17a in parallel as illustrated in FIG. 11(d), a structure of a combination of a rod-shaped positive electrode 17b and a rod-shaped negative electrode 17a disposed in parallel therewith as illustrated in FIG. 12(a), and a combination of a rod shaped positive electrode 17b and two rod-shaped negative electrodes 17a opposing to it as illustrated in FIG. 12(b). A structure of a parallel electrode pair in which planar positive and negative electrodes are placed in parallel may also be employed. Each of these structures of the electrode pair 17 is configured such that the leading end of the negative electrode 17a on the well 21 side extends longer by a predetermined length than the leading end of the positive electrode 17b on the well 21 side.

Figure 13:
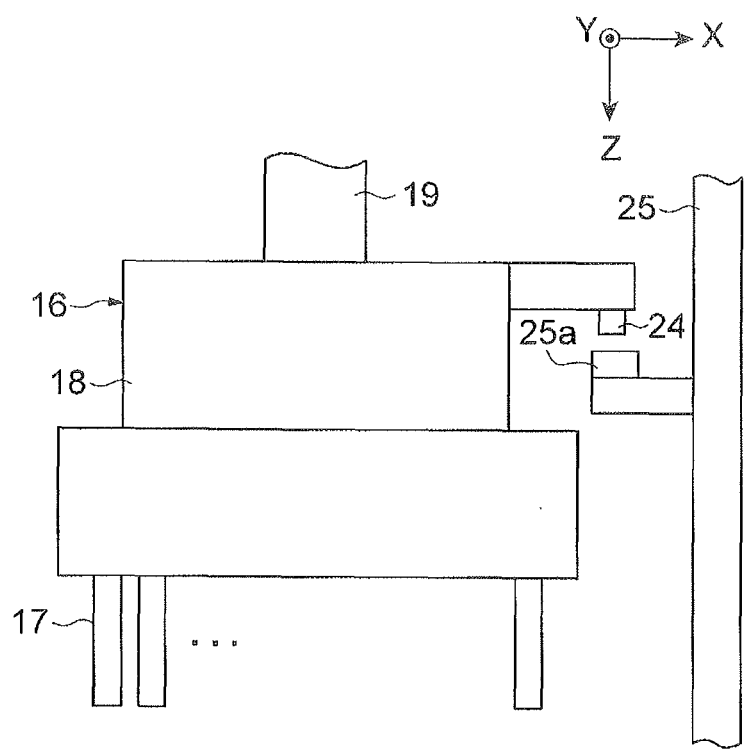
FIG. 13 is a front view illustrating a structure for controlling the position of the electrical stimulator 16 in the cell observation system in accordance with a modified example of the present invention.

While the data analyzer 50 controls the position of the electrical stimulator 16 electronically with reference to the data stored therewithin in the above-mentioned cell observation system 1, members for positional control may be used for mechanical control. FIG. 13 illustrates a structure for controlling the position of the electrical stimulator 16 in the cell observation system in accordance with a modified example of the present invention. A surface on the Z direction side of the base part 18 of the electrical stimulator 16 depicted in this drawing is provided with a button sensor (position detection sensor) 24 for positional detection, while an elongated positional reference member 25 fixed with respect to the dark box 15 (FIG. 1) is disposed on the Z direction side of the button sensor 24. A buffer member 25a is provided at a predetermined position in the Z direction of the positional reference member 25 so as to oppose the button sensor 24. When the data analyzer 50 moves the electrical stimulator 16 in the Z direction such that the electrode pairs 17 thereof are inserted into the wells 21 of the microplate 20 in this cell observation system, contact of the button sensor 24 with the buffer member 25a of the positional reference member 25 is detected, and the movement of the electrical stimulator 16 is stopped in response to the detection. Here, an end face of the buffer member 25a of the positional reference member 25 is set to such a position of the leading end of the button sensor 24 that the negative electrodes 17a of the electrode pairs 17 are in contact with the bottom faces of the wells 21, whereby the position of the electrical stimulator 16 is controlled such that the leading ends of the negative electrodes 17a of the electrode pairs 17 conic into contact with the bottom faces of the wells 21. Providing the positional reference member 25 with the buffer member 25a can mitigate the initial pressure with which the button sensor 24 hits the positional reference member 25, so that the button sensor 24 does not act immediately after the leading ends of the negative electrode pairs 17a come into contact with the bottom faces of the wells 21, whereby the electrical stimulator 16 stops moving after descending by a predetermined length (e.g., on the order of 0.1 mm to 0.2 mm). Therefore, even when the bottom faces of a plurality of wells 21 are located at uneven positions, the leading ends of the negative electrodes 17a can be brought into contact with the bottom faces of all the wells 21.

Though the above-mentioned embodiment is configured such that the microplate 20 to be measured holding the sample S within the microplate stocker 13 is transferred by the microplate transfer mechanism 12 to the measurement position P within the dark box 15 while being mounted on the microplate holder 11, a structure in which the microplate 20 is manually placed at the measurement position P within the dark, box 15 may also be employed.

In the cell observation system 1 and cell observation method by the cell observation system 1 in the above-mentioned embodiment, myocardial cells (cells constituting cardiac muscles) and skeletal muscle cells constituting muscles may be used as the sample S to be measured. The myocardial cells and skeletal muscle cells expand and contract as triggered by action potentials. Here, since calcium ions migrate through a cell membrane from the outside to inside of a cell or vice versa, dyeing calcium ions with a pigment reactive thereto and observing its fluorescence can show how the myocardial cells and skeletal muscle cells expand and contract. While muscle cells within organisms typically expand and contract with the aid of pacemaker cells which control action potentials, myocardial cells and skeletal muscle cells produced from stem cells such as iPS cells and ES cells may lack cells to become a pacemaker or fail to be controlled well. Even such muscle cells can be expanded and contracted when electrical stimulation is imparted thereto from the outside by using the cell observation system 1 so as to control action potentials. There have recently been increasing demands for evaluating drug discovery by using myocardial cells and skeletal muscle cells. In particular, this embodiment performing electrical stimulation from the outside is effective as a technique for evaluating various chemical compounds, since it not only enables usual pacing but also makes it possible to evaluate compounds whose efficacy depends on the beating rate and intentionally cause arrhythmia.

An example using a muscle cell as a subject will now be explained.

Employed as the sample S held within 96 wells 21 of the microplate 20 is one in which a myocardial cell of a heart (ventricle) of a 1-to-4-day-old SD rat was cultivated to $2 \times 10^4$ cells per well. Used as the microplate 20 is one in which the wells 21 were coated with collagen I. The myocardial cell was dyed with a calcium dye (Cal520-AM).

At the position control step (FIG. 5: S03), the data analyzer 50 controls the electrode pairs 17 so that they are placed within the wells 21 holding the myocardial cells. At the light detection step (FIG. 5: S04) thereafter, a voltage is applied to the electrode pairs 17 under the control of the data analyzer 50, so as to impart electrical stimulation to the myocardial cells within the wells 21. Specifically, a pulse voltage in the form of a rectangular wave having a peak value of 5 V and a time width of 5 ms is applied for 5 sec at a repetition frequency of 1 Hz. The repetition frequency is preferably set within the range of 0.5 Hz to 2 Hz. At the same time, the data analyzer 50 acquires moving image data representing a two-dimensional optical image of the microplate 20 for 31 ms per frame, i.e., at a frame rate of 30 frames/sec, while the voltage is applied to the electrode pairs 17. Then, the data analyzer 50 analyzes fluorescence intensity in the analysis region by using the acquired moving image data.

Figure 14:
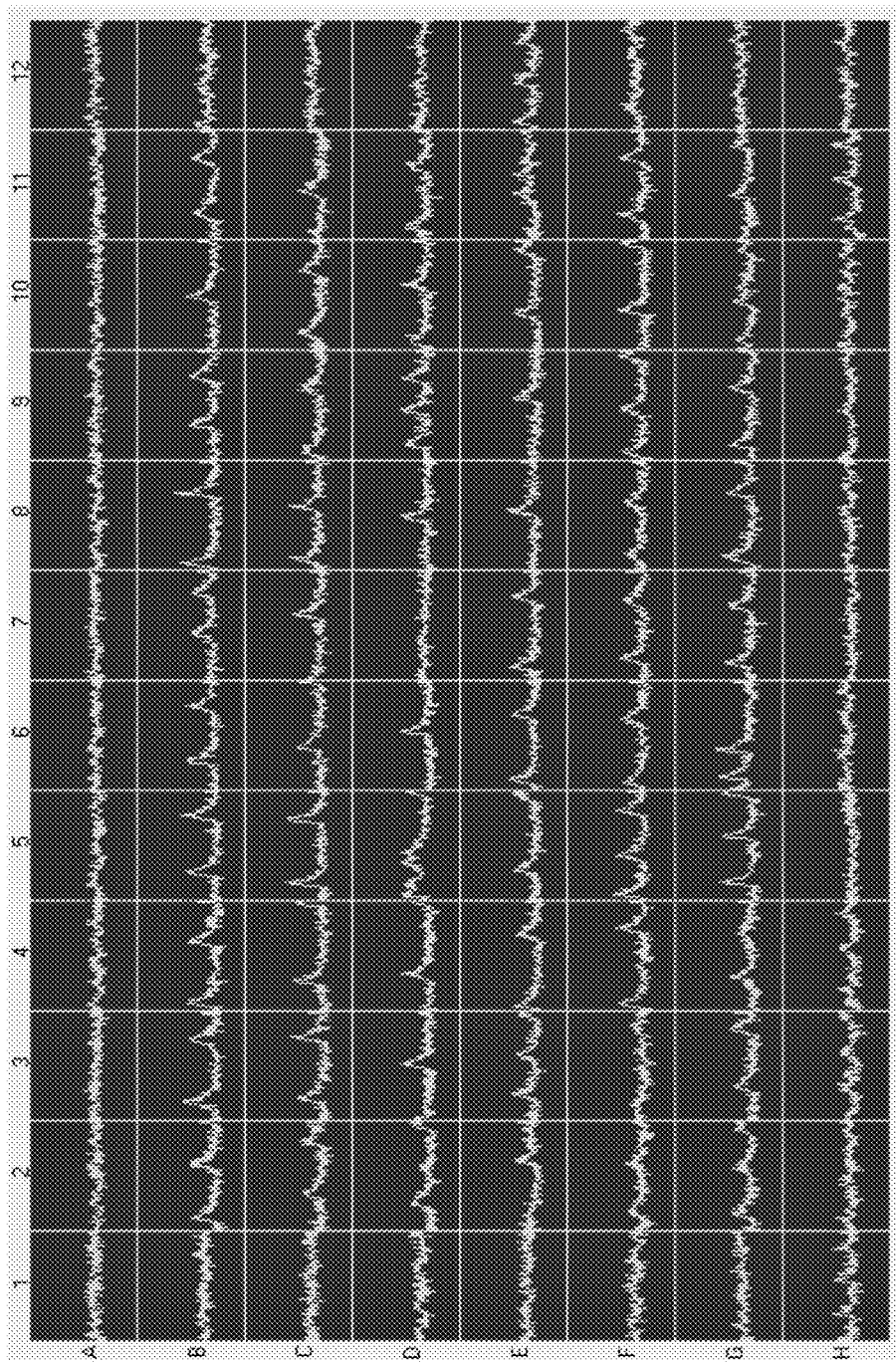
FIG. 14 is a chart illustrating results of measurement of changes with time of average fluorescence intensities in respective analysis regions for two-dimensional optical images in 96 wells 21 acquired when no electrical stimulation was performed in the cell observation system 1.
Figure 15:
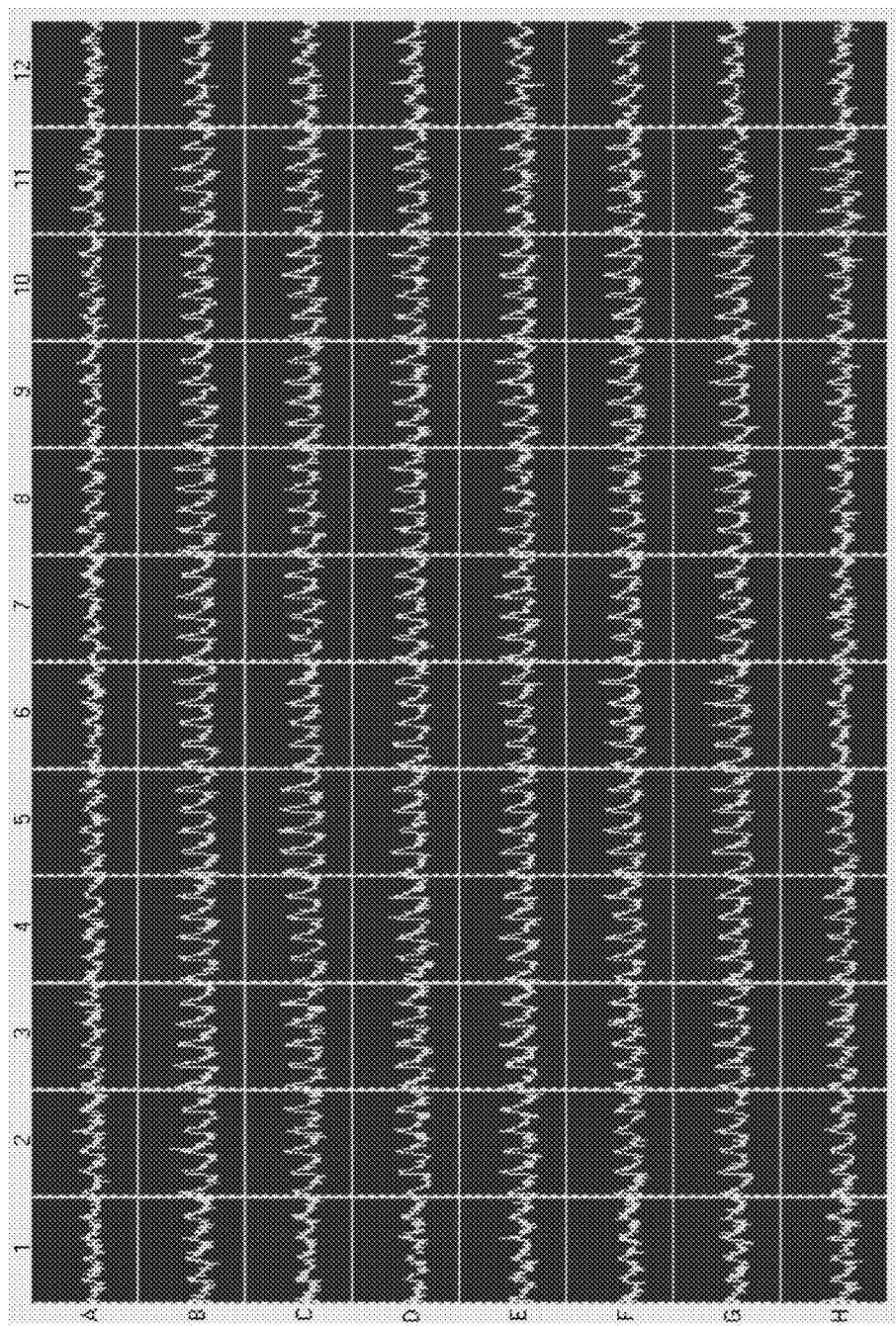
FIG. 15 is a chart illustrating results of measurement of changes with time of average fluorescence intensities in respective analysis regions for two-dimensional optical images in 96 wells 21 acquired when electrical stimulation was performed in the cell observation system 1.

FIGS. 14 and 15 illustrate measurement results of changes with time of average fluorescence intensity in the analysis region of the two-dimensional optical image in each of 96 wells 21 acquired in this example without and with the electrical stimulation by the pulse voltage, respectively. The measurement results for the respective wells 21 are arranged two-dimensionally in columns 1 to 12 and lines A to H. It is seen from the measurement results that, when no pacing with the pulse voltage is performed, cells to become a pacemaker appear to act in a part of the 96 wells so as to change the fluorescence intensity, but there are wells where pacemakers do not work at all. When pacing with the pulse voltage is performed, on the other hand, changes in fluorescence intensity are observed in all of the 96 wells.

Figure 16:
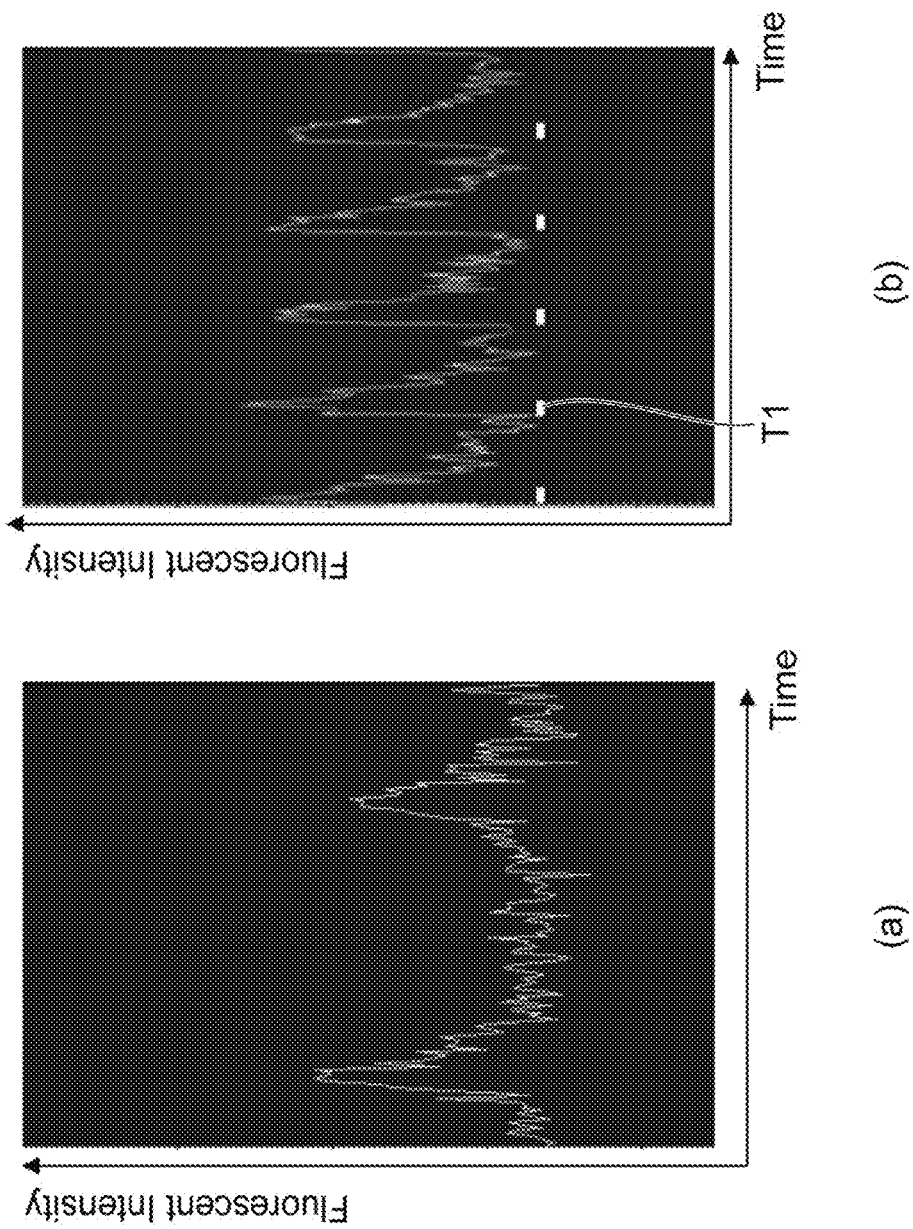
FIG. 16 is a chart illustrating results of measurement corresponding to one well as extracted from the results of measurement in FIGS. 14 and 15.

FIG. 16 illustrates the measurement results of the well at column 3, line B as extracted from those in FIGS. 14 and 15, in which (a) and (b) show the results without and with the electrical stimulation, respectively. Thus, while irregular peaks are observed without pacing, periodical fluorescence peaks are seen in response to timings T1 of electrical stimulation when pacing is performed, which verifies that the above-mentioned cell observation system and cell observation method are effective for pacing myocardial cells.

By randomly applying a rectangular-wave pulse voltage to myocardial cells, the above-mentioned cell observation system and cell observation method are effective in observation in an arrhythmic state.

Preferably, in the above-mentioned cell observation system, the position control unit controls the position such that the leading end of the negative electrode on the holding unit side comes into contact with the bottom face of the holding unit. Employing such a structure can stabilize the distance between the leading end of the positive electrode and sample at a predetermined distance. As a consequence, just providing a simple position control mechanism can stabilize the electric field applied from the electrode pair to the sample.

Preferably, the positive electrode is a rod-shaped electrode. Providing such a rod-shaped electrode can limit a region with a strong electric field on the bottom face of the well to an area near the positive electrode. This can yield highly sensitive observation results concerning the sample.

The negative electrode may be a cylindrical electrode surrounding the positive electrode, a planar electrode facing the positive electrode, or a rod-shaped electrode placed in parallel with the positive electrode.

Preferably, the leading end of the negative electrode extends longer than the leading end of the positive electrode by a length of at least 1 μm but not more than 1.0 mm. This can further stabilize the electric field applied from the electrode pairs to the sample.

Preferably, the position control step controls the position such that the leading end of the negative electrode on the holding unit side comes into contact with the bottom face of the holding unit. This enables simple positional control to stabilize the positional relationship between the electrode pair and sample.

INDUSTRIAL APPLICABILITY

The present invention is used for a cell observation system, electrical stimulation apparatus, and cell observation method for observing a reaction of a sample including a cell in response to electrical stimulation and, with a simple structure, can stabilize an electric field applied to a cell within a plurality of arranged holding units.

REFERENCE SIGNS LIST

1: cell observation system; 11: microplate holder (mounting unit); 16: electrical stimulator; 17: electrode pair; 17*a*: negative electrode; 17*b*: positive electrode; 20: microplate (sample case); 21: well (holding unit); 22: bottom face; 30: position controller (position control unit); 50: data analyzer (position control unit); P: measurement position; S: sample.

The invention claimed is:

1. A system for observing a cell held by a sample case comprising an inner holder that holds a sample including the cell, the system comprising:
a holder configured to hold the sample case;
an electrical stimulator comprising an electrode pair comprising a first electrode and a second electrode; and
a position controller configured to control a position of the electrical stimulator so as to place the electrode pair within the inner holder of the sample case;
wherein a leading end of the second electrode extends longer than a leading end of the first electrode.

2. The system according to claim 1, wherein the position controller controls the position such that the leading end of the second electrode comes into contact with a bottom face of the holding unit.

3. The system according to claim 1, wherein the first electrode comprises a rod-shaped electrode.

4. The system according to claim 3, wherein the second electrode comprises a cylindrical electrode surrounding the first electrode.

5. The system according to claim 3, wherein the second electrode comprises a planar electrode facing the first electrode.

6. The system according to claim 3, wherein the second electrode comprises a rod-shaped electrode placed in parallel with the first electrode.

7. The system according to claim 1, further comprising:
an imaging device comprising a two-dimensional pixel structure and configured to capture light emitted from the sample and output image data; and
a data analyzer coupling the imaging device and configured to receive the moving image data and analyze the moving image data,
wherein the position controller performs such control as to place the electrode pair within the holding unit holding the sample, and
the data analyzer analyzes the optical intensity of an analysis region in a state where a pulse voltage is repeatedly applied to the electrode pair.

8. A method for observing a cell held by a sample case comprising an inner holder that holds a sample including the cell, the method comprising:
- holding the sample case on a holder; and
- controlling a position of an electrical stimulator arranged with an electrode pair comprising a first electrode and a second electrode so as to place the electrode pair within the inner holder of the sample case;
- wherein a leading end of the second electrode extends longer than a leading end of the first electrode.

9. The method according to claim 8, wherein the controlling controls the position such that the leading end of the second electrode comes into contact with a bottom face of the holding unit.

10. The method according to claim 8, further comprising:
- acquiring moving image data of a two-dimensional optical image and outputting the moving image data; and
- analyzing the moving image data,
- wherein the controlling performs such control as to place the electrode pair within the holding unit holding the sample, and
- wherein the analyzing analyzes the optical intensity of an analysis region in a state where a pulse voltage is repeatedly applied to the electrode pair.

11. The method according to claim 8, wherein the cell comprises a muscle cell.

12. The system according to claim 1, wherein the system is configured to observe a muscle cell.

* * * * *